United States Patent [19]

Kahn

[11] Patent Number: 4,857,068
[45] Date of Patent: Aug. 15, 1989

[54] UNIVERSAL SPIKE FOR USE WITH RIGID AND COLLAPSIBLE PARENTERAL FLUID DISPENSING CONTAINER

[75] Inventor: Paul Kahn, San Francisco, Calif.

[73] Assignee: Miles Laboratories, Inc., Elkhart, Ind.

[21] Appl. No.: 223,194

[22] Filed: Jul. 22, 1988

Related U.S. Application Data

[63] Continuation-in-part of Ser. No. 945,269, Dec. 22, 1986, abandoned.

[51] Int. Cl.[4] ............................................. A61B 19/00
[52] U.S. Cl. .................................. 604/405; 604/126; 604/256; 604/411
[58] Field of Search ............................ 604/411–414, 604/405, 251–254, 126, 129, 256

[56] References Cited

U.S. PATENT DOCUMENTS

| | | | |
|---|---|---|---|
| 3,092,106 | 6/1963 | Butler | 604/251 |
| 3,316,908 | 4/1967 | Barke | 604/252 |
| 3,542,240 | 11/1970 | Solowey | 604/411 |
| 3,783,895 | 1/1974 | Weichselbaum | 604/405 |
| 4,010,747 | 3/1977 | Clark et al. | 604/72 |
| 4,262,671 | 4/1981 | Kersten | 604/411 |
| 4,396,016 | 8/1983 | Becker | 604/252 |
| 4,440,207 | 4/1984 | Genatempo et al. | 604/256 |
| 4,508,533 | 4/1985 | Abramson | 604/126 |
| 4,623,343 | 11/1986 | Thompson | 604/405 |
| 4,655,754 | 4/1987 | Richmond et al. | 604/126 |
| 4,750,643 | 6/1988 | Wortrich | 604/411 |

FOREIGN PATENT DOCUMENTS

| | | | |
|---|---|---|---|
| 1125134 | 6/1982 | Canada | 604/251 |
| 1915204 | 11/1969 | Fed. Rep. of Germany . | |

*Primary Examiner*—C. Fred Rosenbaum
*Assistant Examiner*—Mark O. Polatta
*Attorney, Agent, or Firm*—James A. Giblin

[57] ABSTRACT

A universal piercer device for a parenteral fluid dispensing container can be vented and non-vented, alternatively, for use with rigid and collapsible dispensing containers. The universal piercer device includes a venting passage with an air filter, and a reusable, fluid impermeable, pressure-sensitive adhesive seal. The venting passage can include a check-valve.

8 Claims, 2 Drawing Sheets

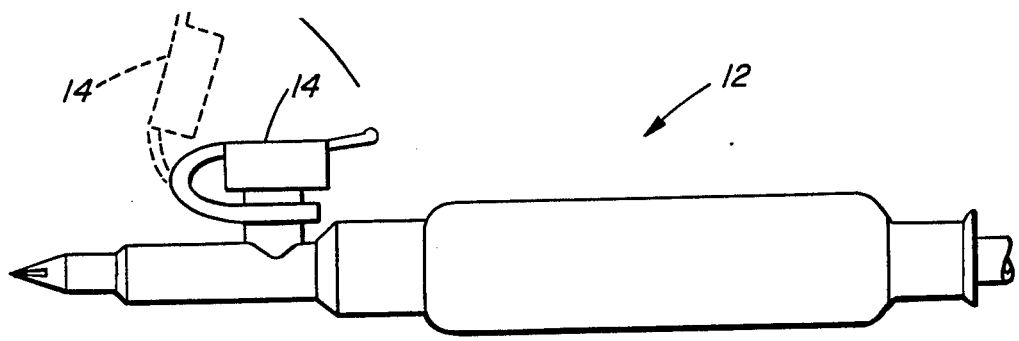
FIG._1. (PRIOR ART)
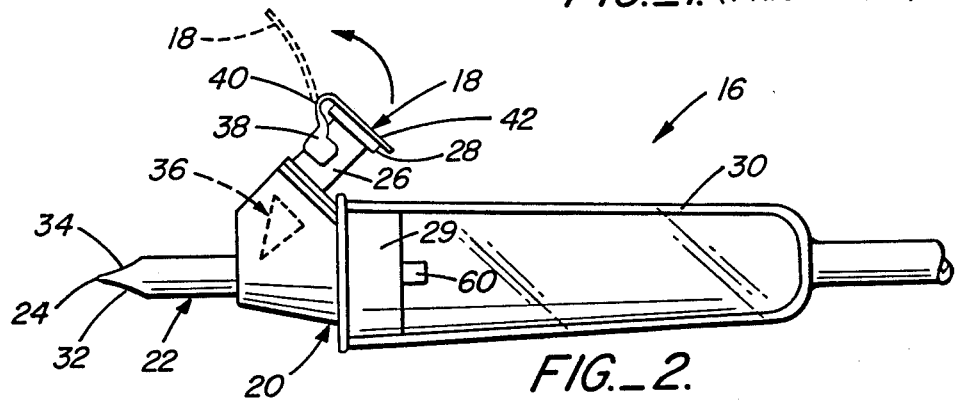
FIG._2.
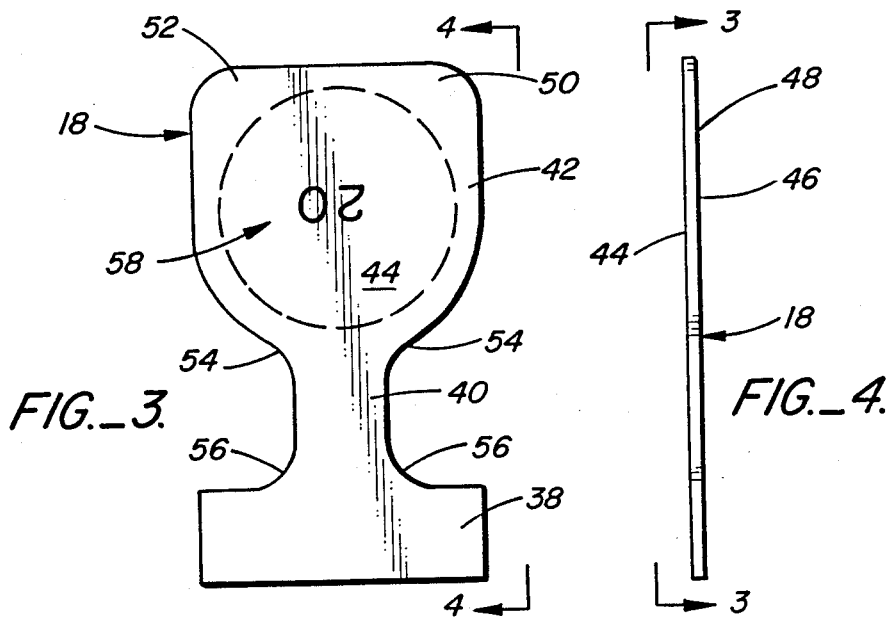
FIG._3.
FIG._4.

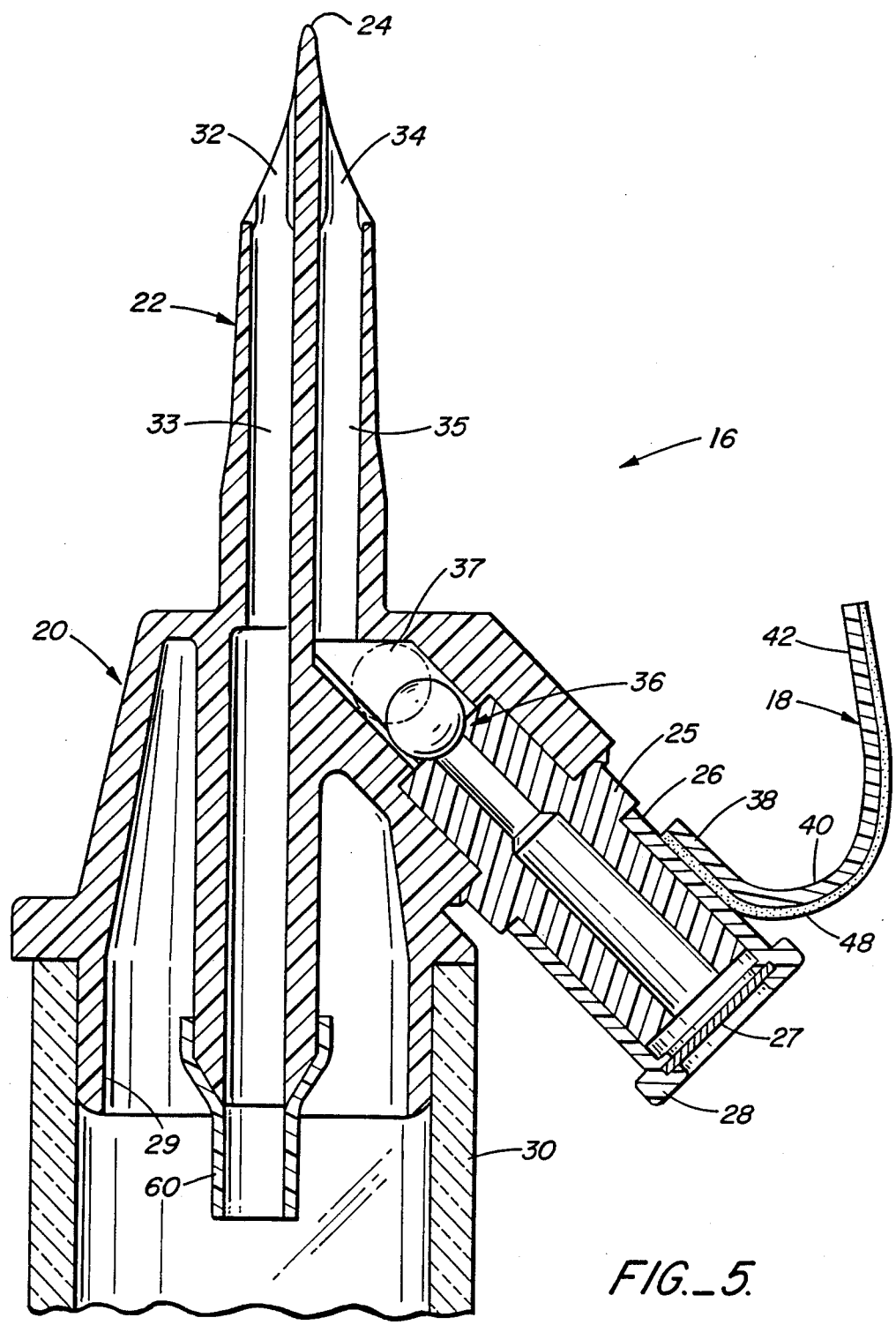
FIG._5.

UNIVERSAL SPIKE FOR USE WITH RIGID AND COLLAPSIBLE PARENTERAL FLUID DISPENSING CONTAINER

This application is a continuation-in-part of application Ser. No. 945,269 filed Dec. 22, 1986, now abandoned.

BACKGROUND OF THE INVENTION

1. Field of the Invention

This invention relates to parenteral fluid dispensing devices and particularly to a universal piercer device that readily can be converted for use with rigid, and collapsible containers.

2. Prior Art

The containers for dispensing parenteral fluids include rigid containers, generally made of glass; and collapsible containers, generally made of plasticized polyvinyl chloride (PVC) or polyolefins. Collapsible containers include bag-type containers and semi-rigid containers. The container includes a puncturable seal for removal of the fluid.

Administration sets are used for transferring fluids from the container into a patient. The patient could include animals, as well as humans. A majority of administration sets are used for intravenous (IV) administration of fluids.

Traditionally, two types of piercing devices or spikes have been used for puncturing the seal of the fluid dispensing containers, a vented spike for rigid fluid dispensing containers and a non-vented spike for collapsible fluid dispensing containers. U.S. Pat. No. 3,868,965 discloses a vented spike. U.S. Pat. No. 3,797,521 discloses a vented spike with a check valve. vented spikes allow air to enter the rigid fluid dispensing container from the atmosphere to replace liquid dispensed from the container. Check valves have been used in combination with vented spikes to prevent leakage or seepage of fluid from the rigid container.

Other known prior art devices, such as a convertible spike of Abbott Laboratories, North Chicago, Ill., include a spike that is inserted to one level for use as a nonvented spike or inserted to a second level for use as a vented spike. This type of system would not permit access to injection or removal of fluid from the container when the nonvented spike level was in use. It would also prohibit piggybacking of a second container.

Collapsible fluid dispensing containers during normal use undergo a pressure differential as the fluid is dispensed which results in a collapsing of the container. Therefore, spikes do not need to include a vent. As a result two types of spikes, vented and non-vented, were required to accommodate rigid and collapsible fluid dispensing containers.

A convertible spike is one that can be used on both rigid and collapsible fluid dispensing containers. Known prior art convertible spikes include a spike with an outlet valve and an air filter that is not removable. Non removable air filters prevent access through the vent passage for injection or removal of fluids or piggybacking of a second container.

Prior art outlet valve include a tethered cap that uses friction and/or interference to seal the outlet valve. These caps are injection molded and therefore increase the cost of the spike. In addition, they can be difficult to remove because of their frictional and/or interference fit.

SUMMARY OF THE INVENTION

The present invention provides a tethered removable sealing member of a fluid impermeable material that includes an adhesive seal. It is easily removed and replaced and reduces the cost of manufacturing. The adhesive seal prevents the flow of air into the collapsible container and prevents the seepage of fluid through the air filter. It is not unusual for a pressure cuff to be applied to a collapsible fluid dispensing container. The externally applied pressure could force fluid past the check valve and through the air filter. The adhesive seal can be used with vented spikes using check valves.

The claimed invention provides a solution to the problem of providing multiple spikes for use with different types of containers. In addition to decreasing cost by providing one device for both purposes, in emergency situations or during disasters, medical personnel do not need to waste time trying to match up spikes with specific types of containers.

Yet another feature of the removable sealing member of the claimed invention is the addition of an indicia for indicating the drop size of the specific universal piercer device since different manufacturers provide devices with different drop sizes. A number such as 12, 15, 20 or 60 would indicate the drop size for the particular set up. Alternatively, other indicia such as a color coded system could be utilized.

The invention will be better understood and additional advantages will become apparent from the description and claims which follow.

BRIEF DESCRIPTION OF THE DRAWING

FIG. 1 is a side view of a prior art spike.

FIG. 2 is a side view of the universal piercer device with tethered sealing member of the claimed invention.

FIG. 3 is a plan view of the reusable sealing member.

FIG. 4 is a lateral view of the sealing member of FIG. 3.

FIG. 5 is an enlarged cross sectional view of the left portion of the spike of FIG. 2, showing an inner check valve referred to generally by the dotted triangle 36 of FIG. 2.

DESCRIPTION OF THE PREFERRED EMBODIMENTS

FIG. 1 illustrates a prior art convertible spike 12 employing an injection molded cap 14 that makes a friction and/or interference fit when in the closed position.

FIGS. 2 and 5 illustrates the universal piercer device 16 employing the sealing tab member 18 of this invention. The universal piercer device 16 comprises base 20 and spike 22. Spike 22 has a sharp end 24 for piercing the closure of parenteral fluid container. Base 20 of universal piercer device 16 includes laterally extending projection 25 in FIG. 2 which is closed by air filter cap 28, with the neck portion 26 of cap 28 extending over the laterally extending projection. In an alternative embodiment, the neck portion 26 of said air filter cap 28 could be inserted inside the laterally extending projection. Air filter cap 28 contains hydrophobic air filter material 27 which is permeable to air but impermeable to liquid at the pressure differentials normally encountered, and serves to filter incoming air for venting the parenteral fluid container. Air filter cap 28 is removable and allows fluid to be injected or removed from the container. It also allows a second container to be piggybacked by connection to said laterally extending projection. Drip chamber 30 is adhesively attached to the base 20 of universal piercer device 16 by a flange 29 (not shown) in FIG. 2. Universal piercer device 16 is typically formed from a moldable plastic such as styrene-acrylonitrile, nylon, or rigid polyvinyl chloride.

Universal piercer device 16 has an opening 32 in spike 22 which defines a fluid passage 35 for communicating with the parenteral fluid container and a discharge opening in base 20. The discharge opening 60 controls the size of the drop of liquid. Discharge opening 60 could, for example, provide a drop size of 12, 15, 20 or 60, drops per ml of fluid. Flow rate is controlled based on the number of drops per minute. Drop size could be indicated on first side 44 to indicate the drop size of the dispensing unit. This could include a number 58 corresponding to the drop size or a color coded system. Universal piercer device 16 also includes a vent passage for venting the parenteral fluid container. The vent passage 35 includes a longitudinally extending portion substantially parallel to the outer wall of spike 22 and substantially parallel to the parenteral fluid passage and has second opening 34 in spike 22 for communicating with the parenteral fluid container. The vent passage 35 also includes laterally extending portion 37 substantially parallel to the walls of extending projection. Said second opening in the vent passage is closed by air filter cap 28. Vent passages are required in piercing devices for use with rigid parenteral fluid containers which do not have a separate vent tube. The universal piercer device 16 can include a check valve 36. The check valve 36 is located inside the vent passage to prevent fluid from leaking or seeping out of the fluid dispensing container vent passage when the air filter is removed, or through the air filter. This generally applies to rigid fluid dispensing containers. To avoid this problem, a sealing member, such as the sealing tab member 18 of the present invention can be used in combination, with a check valve 36 to prevent the leakage or seepage of fluid from rigid container.

Although during normal use, collapsible fluid dispensing containers undergo a pressure differential by collapsing as the fluid is dispensed, it is not unusual for a pressure cuff to be applied to collapsible container. This could cause fluid to be forced through the air filter and leak out of the system. When a pressure cuff is employed on collapsible fluid dispensing containers the externally applied pressure could force fluid past the check valve and through the air filter. Sealing tab member 18 would also prevent the leakage or seepage of fluid from collapsible containers during normal use or with externally applied pressure.

Sealing tab member 18 can provide a seal for nonvented use when adhesively affixed to said air filter cap 28. This would prevent the ingress of air into the container. The potential of air entering the system increases when the fluid level is very low or the container has emptied. The universal piercer device 16 can then be used with collapsible parenteral fluid containers under normal conditions or with externally applied pressure.

FIGS. 3 and 4 illustrate a preferred embodiment of sealing tab member 18 of this invention. The sealing tab member 18 includes a base member 38, a mid portion 40 and a cover portion 42. A first side 44 of said sealing tab member 18 includes a fluid impermeable material such as a flexible, Superstretch polyvinyl chloride, supplied by Avery Co., (Azusa, Calif.). Planar films or generally horizontal planar sheets of fluid impermeable material provide the function of preventing the flow of fluid into or out of the dispensing system. Types of fluid impermeable materials useful in the present invention include metallic foils, polyethylene terephthalates or ionomers, such as Mylar or Surlyn by Dupont, and coated laminates. A second side 46 includes an adhesive for adhering to the surface of said air filter cap 28. Said adhesive portion can be a pressure-sensitive high tack adhesive to allow said cover portion 42 of said sealing tab member 18 to be removed and replaced, alternately. Said adhesive portion also provides a means for affixing said base member 38 to the neck portion 26 of said air filter cap 28 of said universal piercer device 16. The adhesive portion 48 can extend the entire length of said second side 46 or can be limited to the second side 46 of the base member 38 and the cover portion 42. Two or more different types of adhesives can be used on the base member 38 and the cover portion 42. The adhesive can be applied directly to the film or sheet of fluid impermeable material. It can consist of a layer fused to the film or sheet. Types of adhesives could include rubber based adhesives, acrylic based adhesives and silicone adhesives. This adhesive attachment provides a means of removing and replacing a seal that is much easier to use than prior art closures which include lip portions to provide friction or interference fit.

The cover portion 42 includes a tab portion 50 for removing and replacing said sealing tab member 18. The tab portion 50 can be formed by constructing said cover portion 42 of said sealing member 18 to sufficiently overlap the outer surface of said air filter cap 28 to provide at least one tab portion 50. In the preferred embodiment, a second tab portion 52 is provided.

The base member 38 can be designed to partially encircle said neck portion 26 of said air filter cap for attachment or tethering as shown in FIG. 2 to accommodate mechanical attachment of said sealing tab member 18 to said universal piercer device 16. Alternatively, said base member 38 could partially or totally encircle or even overlap when affixed or tethered to said neck portion 26. The mid portion 40 can include curved portions 54 and 56 to distribute any stress applied to said sealing tab member 18 during its removal and replacement. Although it is understood that the curved portions 54 and 56 could include right angles, it is felt that the curved portions of the preferred embodiment would decrease the likelihood of tearing during use.

It is understood that an important aspect of this invention is the ease of manufacture and attachment of said sealing tab member 18. Said sealing tab member 18 can be manufactured from a generally flat, layer of adhesive backed material. The fluid impermeable material could include more than one layer and could be a composite of layers having the required function. Said sealing tab member 18 could be made in continuous strips to avoid waste of materials and to accommodate mechanical application.

Given the above disclosure, it is thought variations will occur to those skilled in the art. Accordingly, it is intended that the above example should be construed as illustrative and the scope of the invention should be limited only by the following claims.

I claim:

1. A universal piercer device for a parenteral fluid dispensing container comprising:
   a spike having a base and a piercing member with a sharp end for piercing the closure of a parental fluid container;

said spike including means for defining first and second conduits extending downwardly when said container is in dispensing position;

said first fluid conduit being adapted for dispensing fluid from said container;

said second fluid conduit having a non-removable internal check valve for allowing fluid to flow into said container under a pressure greater than that in said container adjacent said second conduit, but preventing the reverse flow of fluid from said container;

said second conduit including a vent passage and a removable air filter for venting said parenteral fluid container when the filter is present and allowing fluid to be injected into or removed from the container when the filter is removed;

and a removable sealing member for unsealing said vent passage when the device is used with a rigid container.

2. The universal piercer device of claim 1 wherein said sealing member comprises a film that does not permit passage of fluid therethrough.

3. The universal piercer device of claim 2 wherein the said fluid impermeable seal is selected from the group consisting of flexible polyvinylchloride, coated laminates, metallic foils, polyethylene terephthalates, and ionomoers.

4. The universal piercer device of claim 2 wherein an adhesive layer is added to said film.

5. The universal piercer device of claim 4 wherein said adhesive portion is a pressure-sensitive high tack adhesive selected from the group consisting of rubber based adhesives, acrylic based adhesives and silicon based adhesives.

6. The universal pierce of claim 1 wherein said sealing member is tethered to said universal piercer device.

7. The universal piercer device of claim 1 wherein said sealing member includes a tab portion for removing and replacing said member.

8. The universal piercer device of claim 7 wherein said tab portion is formed by constructing said sealing member to sufficiently overlap the outer surface of said vent passage to provide at least one tab portion.

* * * * *